United States Patent [19]

Harita et al.

[11] 4,070,484
[45] Jan. 24, 1978

[54] ANTIALLERGIC COMPOSITION CONTAINING AROMATIC CARBOXYLIC AMIDE DERIVATIVES AND METHOD OF USING THE SAME

[75] Inventors: Kozaburo Harita, Hongo; Yukiyoshi Ajisawa, Okaya; Kinji Iizuka; Yukihiko Kinoshita, both of Matsumoto; Tetsuhide Kamijo, Shiojiri; Michihiro Kobayashi, Toyoshina, all of Japan

[73] Assignee: Kissei Pharmaceutical Co., Ltd., Matsumoto, Japan

[21] Appl. No.: 752,885

[22] Filed: Dec. 21, 1976

Related U.S. Application Data

[63] Continuation of Ser. No. 559,041, July 25, 1975, abandoned, which is a continuation-in-part of Ser. No. 434,252, Jan. 17, 1976, Pat. No. 3,940,422.

[30] Foreign Application Priority Data

Jan. 18, 1973  Japan .................................. 48-7359

[51] Int. Cl.² ................ A61K 31/195; A61K 31/335; A61K 31/36
[52] U.S. Cl. .................................. 424/319; 424/278; 424/282
[58] Field of Search ........................ 424/319, 282, 278

[56] References Cited

U.S. PATENT DOCUMENTS 3,655,743  4/1972  Nickl et al. ..................... 424/319
3,758,528  9/1973  Malen et al. .................... 424/319

OTHER PUBLICATIONS

Nossier et al. - J. Chem. U.A.R. (1969), vol. 12, No. 1, pp. 57-68.
Seka et al. - Monatsh, 53-54, (1929), pp. 471-484.
Karmarkar et al., J. Indian Chem. Soc., vol. 30, (1953), pp. 689-694.
Nossier et al. - U.A.R. J. Chem., vol. 13, No. 4, (1970), pp. 379-390.

Primary Examiner—Sam Rosen

[57] ABSTRACT

Aromatic carboxylic amides of the general formula:

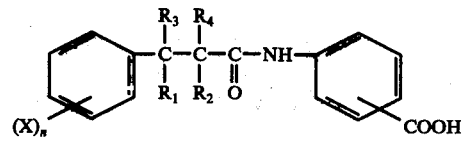

wherein each of $R_1$ and $R_2$ is a hydrogen atom or an alkyl group having 1-4 carbon atoms, $R_3$ and $R_4$ are hydrogen atoms or together form another chemical bond, each X is a hydroxyl group, a halogen atom, an alkyl group having 1-4 carbon atoms and an alkoxyl group containing 1-4 carbon atoms, and may be the same or different, and $n$ is an integer of 1-3, provided that when two Xs are alkyl or alkoxyl groups, the alkyl groups thereof may be connected together into an alkylene group, and the pharmaceutically acceptable salts thereof, possess a strong antiallergic action and are thus useful for treatment of asthma, hay fever, urticaria and atopic dermatitis.

20 Claims, No Drawings

ANTIALLERGIC COMPOSITION CONTAINING AROMATIC CARBOXYLIC AMIDE DERIVATIVES AND METHOD OF USING THE SAME

This application is a continuation of Ser. No. 559,041, filed July 25, 1975, and now abandoned, which, in turn, is a continuation-in-part of Ser. No. 434,252, filed Jan. 17, 1974, and now U.S. Pat. No. 3,940,422.

BACKGROUND OF THE INVENTION

This invention relates to nuclear-substituted cinnamoylaminobenzoic acid and hydrocinnamoylaminobenzoic acid derivatives exhibiting a strong antiallergic action when administered orally to mammalia including humans and to methods and compositions for using the same.

Up to now, disodium cromoglycate was only one drug that inhibits the disruption of mast cells and release therefrom of chemical mediators. However, this compound loses its pharmacological effect when administered orally, which limits its range of usefulness. Thus, development of an antiallergic agent which can display a sufficient therapeutic effect and be administered orally has long been demanded in the field of medicine.

On the other hand, nuclear-unsubstituted cinnamoylaminobenzoic acid was already synthetized by Reinicke and publicly known (Liebig's Annalen der Chemie, Vol. 341, pages 94-96). However, this compound shows only very weak antiallergic effect, when administered orally to mammalia, and thus has little value as a practical medicament.

BRIEF SUMMARY OF THE INVENTION

Accordingly, it is an object of this invention to provide a method for obtaining a strong antiallergic action particularly by oral administration to mammalia including humans and a pharmaceutical composition useful therein.

Other objects, features and advantages of this invention will become apparent as the description proceeds.

The attached single drawing is a graph showing the change in physiological state with lapse of time when a compound of this invention is administered to rats with experimental induced asthma.

DETAILED DESCRIPTION OF THE INVENTION

It has now been found that a compound of the general formula:

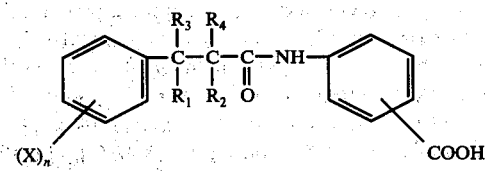

wherein each of $R_1$ and $R_2$ is a hydrogen atom or an alkyl group having 1-4 carbon atoms, $R_3$ and $R_4$ are each a hydrogen atom or together form another chemical bond, each X is a hydroxyl group, a halogen atom, an alkyl group having 1-4 carbon atoms and an alkoxyl group having 1-4 carbon atoms and may be the same or different, and $n$ is an integer of 1-3, provided that when two Xs are alkyl or alkoxyl groups, the alkyl groups thereof may be connected together into an alkylene group, can inhibit an experimentally induced anaphylaxis (for example, inflammation of skin caused by an antigen-antibody reaction between reagin and its peculiar antigen) when administered orally to patients. It has also been found that these compounds inhibit disruption of mast cells caused by a certain kind of an antigen-antibody reaction (for example, an antigen-antibody reaction between a reaginic antibody and its peculiar antigen) and the subsequent release of chemical mediators from the mast cells.

In view of these characteristic properties, it is expected that these compounds possess an antiallergic action and are effective for the therapeutical treatment of diseases caused by allergies, such as asthma, hay fever, urticaria and atopic dermatitis. In fact, they were found to be effective to alleviate symptoms in respiration and blood pressure observed in experimentally induced asthma of mammalia.

The compounds of this invention are characterized by the presence of at least one substituent selected from hydroxyl alkyl and alkoxyl groups and halogen atoms as a nuclear substituent. If the compounds are free of any such substituent, they become weak in antiallergic action and less valuable for practical use. In case the nuclear substituent is one or more alkyl or alkoxyl groups, they may be linear or branched. Within the range of 1–4 carbon atoms in such groups, no significant change was found in pharmacological effect. Methylenedioxycinnamoylaminobenzoic acid also possesses a strong antiallergic action. The halogen atoms as nuclear substituents may be chlorine atoms, fluorine atoms and bromine atoms. Compounds having such nuclear halogen atoms are similarly strong in anti-allergic action. The number of the nuclear substituents is limited to 1–3. In general, however, pharmacological activity becomes higher as the number of nuclear substituents increases. Compounds carrying as nuclear substituent a hydrophilic group such as a 2,3-dihydroxypropoxy group or a carboxymethoxy group are extremely weak in pharmacological activity.

In the compounds of this invention, the carboxyl group in the aminobenzoic acid residue may be in any of the 2-, 3- and 4-positions. Salts of compounds having this carboxyl group, such as alkali metal salts, are as high in pharmacological effect as the corresponding compounds having free acid groups, while derivatives in the form of esters of a lower alcohol were found to be inferior in pharmacological activity.

Compounds of the general formula (I) can be prepared, for example, by a process wherein a reactive functional derivative of an aromatic carboxylic acid of the general formula:

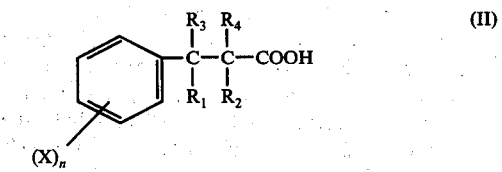

wherein $R_1$, $R_2$, $R_3$, $R_4$, X and $n$ have the same meanings as given above, is reacted with an aminobenzoic acid of the formula:

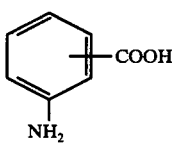

Alternatively, an aromatic carboxylic acid or a reactive functional derivative thereof of the above general formula (II) can be reacted with an aminobenzoic ester of the general formula:

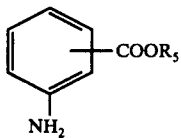

wherein $R_5$ is an alkyl group having 1–4 carbon atoms, to provide an aromatic carboxylic amide derivative of the general formula:

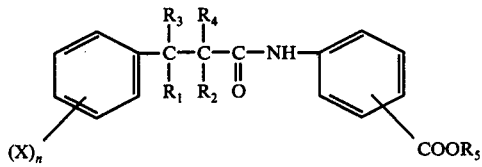

wherein $R_1$, $R_2$, $R_3$, $R_4$, $R_5$, X and $n$ have the same meanings as given above, and then this derivative is hydrolyzed to convert the ester into a free acid.

Furthermore, the compounds of the general formula (I) can be prepared by halogenating a carboxylic acid of a hemiester of malonic acid, reacting the halogenated product in an inert organic solvent such as chloroform with an aminobenzoic acid of the general formula (III) or an ester of the general formula (IV) in the presence of a base, such as a tertiary amine, hydrolyzing the resulting product to form an amidocarboxylic acid and condensing the amidocarboxylic acid according to the Knoevenagel reaction with a nuclear-substituted benzaldehyde corresponding to a carboxylic acid of the general formula (II).

The aromatic carboxylic acids of the above general formula (II) are known compounds and can easily be prepared according to methods disclosed in literature. Aromatic carboxylic acids having an unsaturated bond involve the two isomers, i.e., cis-form and trans-form, and either may be employed for the process of this invention. Examples of the aromatic carboxylic acids of the general formula (II) include aromatic saturated carboxylic acids, such as 2-, 3- or 4-methylhydrocinnamic acid, 2-, 3- or 4-ethylhydrocinnamic acid, 2-, 3- or 4-propylhydrocinnamic acid, 2-, 3- or 4-hydroxyhydrocinnamic acid, 2-, 3- or 4-methoxyhydrocinnamic acid, 2-, 3- or 4-ethoxyhydrocinnamic acid, 2-, 3- or 4-chlorohydrocinnamic acid, 2-, 3- or 4-bromohydrocinnamic acid, 2-, 3- or 4-fluorohydrocinnamic acid, 2,3-dimethylhydrocinnamic acid, 3,4-methylenedioxyhydrocinnamic acid, α-methyl-4-ethylhydrocinnamic acid and β-ethyl-2-chlorohydrocinnamic acid; and aromatic unsaturated carboxylic acids, such as 2-, 3- or 4-methylcinnamic acid, 2-, 3- or 4-ethylcinnamic acid, 2-, 3- or 4-propylcinnamic acid, 2-, 3- or 4-butylcinnamic acid, 2-, 3- or 4-hydroxycinnamic acid, 2-, 3- or 4-methoxycinnamic acid, 2-, 3- or 4-ethoxycinnamic acid, 2-, 3- or 4-propoxycinnamic acid, 2-, 3- or 4-chlorocinnamic acid, 2-, 3- or 4-fluorocinnamic acid, 2-, 3- or 4-bromocinnamic acid, 2-methyl-3-ethylcinnamic acid, 3,4-dimethylcinnamic acid, 2,3-dimethoxycinnamic acid, 3,4-dimethoxycinnamic acid, α-methyl-3,4-dimethoxycinnamic acid, β-methyl-3,4-dimethoxycinnamic acid, 3,4-diethoxycinnamic acid, 2,4,5-trimethoxycinnamic acid, 2,4-dichlorocinnamic acid and 3,4-methylenedioxycinnamic acid. In the process of this invention, reactive functional derivatives of such aromatic carboxylic acids are used as a starting material. Examples of such derivatives include carboxylic acid derivatives, such as acid halides and a reaction product of such carboxylic acid. These reactive functional derivatives can easily be derived from the aromatic carboxylic acids of the general formula (II) according to a usual technique known in this art. For example, the acid chlorides can easily be obtained by refluxing for several hours the aromatic carboxylic acid with thionyl chloride in the absence of any solvent or in dry benzene. The mixed acid anhydrides can be obtained, for example, by reaction with a chloroformic ester.

Any of anthranilic acid, m-aminobenzoic acid and p-aminobenzoic acid can be used as the aminobenzoic acid of the general formula (III). Any of anthranilic esters, m-aminobenzoic esters and p-aminobenzoic esters can be used as an aminobenzoic ester of the general formula (IV).

The above-mentioned amidation can be carried out according to methods known per se. For example, when an acid halide is used as the reactive functional derivative, the acid halide can be reacted in an inert solvent with an aminobenzoic acid of the general formula (III) or a derivative thereof of the general formula (IV) in the presence of a basic substance. In this case, a tertiary organic base such as trimethylamine, triethylamine or pyridine or an inorganic base such as caustic alkali, sodium carbonate or potassium carbonate is used as the basic substance. Adequate as the inert solvent are chloroform, methylene chloride, acetone, benzene, toluene, tetrahydrofuran, dioxane and dimethylformamide.

Instead of using such a basic substance, the reaction may be carried out by using a compound of the general formula (III) in an excess amount, e.g., more than 2 molar proportion to the compound of the general formula (II).

The process of this invention is carried out preferably by dissolving a compound of the general formula (III) in a mixture of chloroform and pyridine respectively in amounts of 5–40 times and 2–15 times as much as the amount of the compound of the general formula (II), adding a solution of a compound of the general formula (II) in dry chloroform to the mixture under cooling and stirring and then refluxing the whole for several hours.

The reaction product is concentrated under reduced pressure and the residue is poured into water. Hydrochloric acid is then added to the aqueous mixture to make it weakly acidic. The precipitated crystals are collected by filtration and then recrystallized from an adequate organic solvent to obtain the end product.

In case of compound of the general formula (II) is an aromatic carboxylic acid carrying a hydroxyl group on the benzene nucleus, such compound is preferably protected in the hydroxyl group with acetyl group or the like prior to the reaction with a compound of the general formula (III). This protective group can be removed in the usual manner.

The resulting compound (I) carrying a carboxyl group can be converted according to usual methods to a physiologically acceptable salt thereof. For example, an aqueous solution of caustic soda in an equimolar amount can be added to an alcoholic solution of a compound of the general formula (I) and the mixture is warmed for an adequate period of time whereby the compound can easily be converted into its sodium salt. As examples of such physiologically acceptable salts there can be mentioned, in addition to the sodium salt, alkali metal salts, such as the potassium salt and lithium salt, alkali earth metal salts, such as the magnesium salt and calcium salts, salts with organic amines, such as piperidine, triethanolamine and diethylaminoethylamine, and the ammonium salt.

The aromatic carboxylic amide derivatives of this invention possess a special activity to the effects of an antigen-antibody reaction. Thus, they can be used widely as therapeutic medicaments for diseases caused by allergies.

This invention will be illustrated in more detail by way of examples wherein none of the melting points of the products have been corrected.

EXAMPLE 1

In a mixture of 20 ml of chloroform and 10 ml of pyridine were dissolved 2.6 g of 4-aminobenzoic acid. To this mixture were added dropwise under cooling 20 ml of chloroform containing 3.2 g of 4-acetoxycinnamoyl chloride. The mixture was heated under reflux for 2 hours and the reaction mixture was concentrated under reduced pressure. The residue was poured into water and hydrochloric acid was then added to make the liquid weakly acidic. The precipitated crystals were collected by filtration and recrystallized from alcohol to yield 2.9 g of 4-(4'-acetoxycinnamoyl-amino)-benzoic acid. M.P. = 305°-307° C (with decomposition).

A mixture of 2.7 g of 4-(4'-acetoxycinnamoylamino)-benzoic acid and 50 ml of a 10% aqueous solution of sodium hydroxide was warmed for one hour, cooled and then weakly acidified with hydrochloric acid. The precipitated crystals were collected by filtration and recrystallized from aqueous alcohol whereby 1.75 g of 4-(4'-hydroxycinnamoylamino)benzoic acid were obtained. M.P. = 306°-307° C (with decomposition).

Elementary analysis as $C_{16}H_{13}O_4N$

|  | C | H | N |
|---|---|---|---|
| Calc. | 67.84% | 4.63% | 4.95% |
| Found | 67.69 | 4.56 | 4.72 |

IR-absorption spectra (KBr)
  $\nu$CO: 1690, 1670 cm$^{-1}$
NMR spectra (d$_6$ - DMSO)
  δ6.75, 7.58 (q, 2H J = 17 Hz, olefinic proton)
  6.90, 7.52 (q, 4H J = 8 Hz, hydroxyl group-substituted aromatic ring proton)
  7.87, 7.96 (q, 4H J = 9 Hz, amido group-substituted aromatic ring proton) 10 4 (s, 1 H, carboxylic acid proton)
Mass spectra
  M$^+$ 283,
  m/e 238, 147, 119.

In 100 ml of warmed ethanol were dissolved 1.42 g of 4-(4'-hydroxycinnamoylamino)benzoic acid. To this solution was added a solution of 0.21 g of sodium hydroxide in 3 ml of water and the mixture was warmed for 30 minutes, cooled and then filtered to collect crystals precipitated. 1.20 Grams of sodium salt of 4-(4'-hydroxycinnamoylamino)benzoic acid were thus obtained.

The following compounds can be prepared in a similar manner:

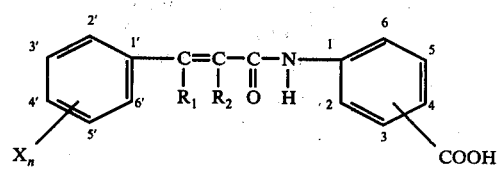

| Comp No. | n | X | R$_1$ | R$_2$ | Pos. COOH | M.P. (° C) | Recrys. Solvent |
|---|---|---|---|---|---|---|---|
| 1 | 1 | 4'-OH | H | H | 2 | 220.5–221.5 | Aq.Alc. |
| 2 | 1 | 4'-OH | H | H | 4 | 306–307 (w/decomp.) | " |
| 3 | 1 | 2'-OH | H | H | 2 | 230–231 | " |
| 4 | 1 | 2'-OH | H | H | 3 | 267–268 | " |
| 5 | 2 | 2'-OH 3'-OMe | H | H | 2 | 206–208 | " |
| 6 | 2 | 2'-OH 3'-OMe | H | H | 4 | 307–307.5 (w/decomp.) | " |
| 7 | 2 | 4'-OH 3'-OMe | H | H | 2 | 230–232 | Alcohol |
| 8 | 2 | 4'-OH 3'-OMe | H | H | 3 | 238–239.5 | Aq.Alc. |
| 9 | 2 | 3'-OH 4'-OH | H | H | 2 | 204–206 (w/decomp.) | " |
| 10 | 3 | 2'-Br 4'-OH 5'-OMe | H | H | 2 | 249–250 | " |
| 11 | 2 | 4'-OH 3'-OMe | H | H | 4 | 250–251 | " |

EXAMPLE 2

In a similar manner except that 3-methoxy-4-acetoxyhydrocinnamoyl chloride was used in place of the 4-acetoxycinnamoyl chloride used in Example 1 for reaction with 3-aminobenzoic acid and the reaction product was hydrolyzed, 3-(3'-methoxy-4'-hydroxyhydrocinnamoylamino)benzoic acid was obtained. After recrystallization from an aqueous alcohol, this product had a melting point of 218°-220° C.

EXAMPLE 3

4.3 Grams of 4-aminobenzoic acid were dissolved in a mixture of 100 ml of chloroform and 19 g of pyridine. To this mixture were added dropwise under cooling 100 ml of a dry chloroform solution containing 5.4 g of 3,4-dimethoxycinnamoyl chloride. The mixture was heated under reflux for 1.5 hours and the reaction mixture was then concentrated under reduced pressure. The residue was poured into water and hydrochloric acid was then added to make the liquid weakly acidic. The precipitated crystals were collected by filtration and recrystallized from an alcohol whereby 5.6 g of 4-(3',4'-dimethoxycinnamoylamino)benzoic acid were obtained. M.P. = 267°-9° C.

Elementary analysis as $C_{18}H_{17}O_5N$

|  | C | H | N |
|---|---|---|---|
| Calc. | 66.05% | 5.24% | 4.28% |
| Found | 66.00 | 5.12 | 4.14 |

IR-absorption spectra (KBr)

νCO: 1690, 1665 cm$^{-1}$
νNH: 3320 cm$^{-1}$
NMR spectra (d$_6$ - DMSO)
δ6.78, 7.62 (q, 2H, J = 16 Hz olefinic proton)
7.0–7.3 (m, 3H, methoxy-substituted aromatic ring proton)
7.85, 7.97 (q, 4H, J = 9 Hz, amido-substituted aromatic ring proton)
10.4 (s, 1H, carboxylic acid proton)
11.5–12.7 (broad, 1H, amido proton)
3.81, 3.83 (s, s, 6H, methoxy proton)
Mass spectra
M$^+$ 327
m/e 282, 191, 163.

1.5 Grams of 4-(3',4'-dimethoxycinnamoylamino)benzoic acid were dissolved in 150 ml of warmed ethanol and an aqueous alcoholic solution (ethanol 2: water 1) of an equimolar amount of sodium hydroxide was added whereby white crystals precipitated out. The crystals were collected by filtration and dried under reduced pressure to obtain 1.0 g of sodium salt of 4-(3',4'-dimethoxycinnamoylamino)benzoic acid.

In a similar manner, the following compounds can be prepared:

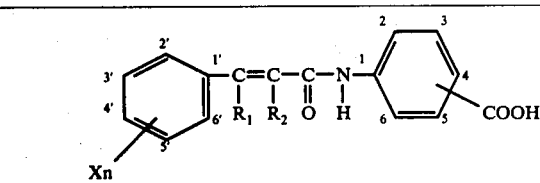

| Comp No. | n | X | R$_1$ | R$_2$ | Pos. COOH | M.P. (° C) | Recrys. Solvent |
|---|---|---|---|---|---|---|---|
| 12 | 1 | 4'-OMe | H | H | 2 | 195–198 | Aq.Alc. |
| 13 | 1 | 4'-OMe | H | H | 4 | 292–294 | Alcohol |
| 14 | 1 | 3'-OMe | H | H | 2 | 183–185 | Aq.Alc. |
| 15 | 1 | 3'-OMe | H | H | 3 | 213–216 | " |
| 16 | 1 | 4'-OMe | CH$_3$ | H | 2 | 171–172 | " |
| 17 | 1 | 4'-OMe | CH$_3$ | H | 4 | 262–263 | Alcohol |
| 18 | 1 | 4'-OMe | H | CH$_3$ | 2 | 188–191 | Aq.Alc. |
| 19 | 1 | 4'-OMe | H | CH$_3$ | 3 | 244–246 | Alcohol |
| 20 | 1 | 4'-Cl | H | H | 2 | 195–203 | Aq.Alc. |
| 21 | 1 | 4'-Cl | H | H | 4 | 332–335 (w/decomp.) | " |
| 22 | 1 | 2'-Cl | H | H | 2 | 184.5–188.5 | " |
| 23 | 1 | 2'-Cl | H | H | 3 | 289–291 | " |
| 24 | 1 | 4'-Cl | CH$_3$ | H | 2 | 183–185 | " |
| 25 | 1 | 4'-Cl | CH$_3$ | H | 4 | 294–295 | Alcohol |
| 26 | 1 | 4'-Cl | H | CH$_3$ | 3 | 244–244.5 | " |
| 27 | 1 | 4'-Cl | H | CH$_3$ | 2 | 208.5–210.5 | Chlo. |
| 28 | 1 | 4'-F | H | H | 2 | 200–201.5 | Alcohol |
| 29 | 1 | 3'-F | H | H | 2 | 194–195.5 | " |
| 30 | 1 | 2'-F | H | H | 2 | 193–194.5 | " |
| 31 | 2 | 2'-OMe 3'-OMe | H | H | 2 | 198.5–200 | Aq.Alco. |
| 32 | 2 | 2'-OMe 3'-OMe | H | H | 4 | 261–263.5 | Alcohol |
| 33 | 2 | 3'-OMe 4'-OMe | H | H | 2 | 211–213 | Chlo. |
| 34 | 2 | 3'-OMe 4'-OMe | H | H | 3 | 225–226 | Alcohol |
| 35 | 2 | 3'-OMe 4'-OMe | H | H | 4 | 267–269 | Alcohol |
| 36 | 2 | 3'-OMe 4'-OMe | CH$_3$ | H | 2 | 173–75 | Aq.Alc. |
| 37 | 2 | 3'-OMe 4'-OMe | CH$_3$ | H | 3 | 163–164 | " |
| 38 | 2 | 3'-OMe 4'-OMe | CH$_3$ | H | 4 | 241–243 | Alcohol |
| 39 | 2 | 3'-OMe 4'-OMe | H | CH$_3$ | 2 | 169–172 | Aq.Alc. |
| 40 | 2 | 3'-OMe 4'-OMe | H | CH$_3$ | 3 | 203.5–204.5 | " |
| 41 | 2 | 3'-OMe 4'-OMe | H | CH$_3$ | 4 | 225.5–227.5 | |
| 42 | 1 | 4'-CH$_3$ | H | H | 2 | 210.5–213 | Aq.Alc. |
| 43 | 1 | 4'-CH$_3$ | H | H | 4 | 308–310 | " |
| 44 | 1 | 4'-Cl | C$_2$H$_5$ | H | 2 | 201–204 | " |
| 45 | 1 | 4'-OMe | H | C$_2$H$_5$ | 4 | 220–221.5 | " |
| 46 | 1 | 4'-Br | H | H | 2 | 222–225 | " |
| 47 | 1 | 4'-Br | H | H | 4 | >330 | Alcohol |
| 48 | 2 | 3'-OEt 4'-OEt | H | H | 2 | 185–187 | Aq.Alc. |
| 49 | 2 | 3'-OEt 4'-OEt | H | H | 4 | 253–256 | " |
| 50 | 2 | 4'-OEt 3'-OMe | H | H | 2 | 210.5–212.5 | " |
| 51 | 2 | 4'-OEt 3'-OMe | H | H | 3 | 219–222 | " |
| 52 | 3 | 2'-OMe 4'-OMe 5'-OMe | H | H | 2 | 206–208 | " |
| 53 | 2 | 3',4'-methylenedioxy | H | H | 2 | 209–210.5 | Alcohol |
| 54 | 2 | 4'-O-n-Pro 3'-OMe | H | H | 2 | 172–177 | Chlo. |

-continued

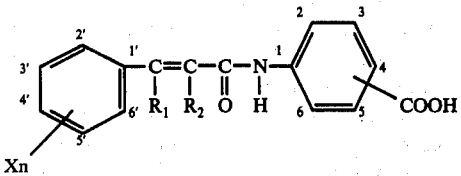

| Comp No. | n | X | $R_1$ | $R_2$ | Pos. COOH | M.P. (° C) | Recrys. Solvent |
|---|---|---|---|---|---|---|---|
| 56 | 2 | 4'-O-i-Pro 3'-OMe | H | H | 2 | 76–78 | " |
| 57 | 1 | 3-O-i-Pro | H | H | 2 | 121–124 | Benz/Pet. Ether |
| 58 | 1 | 4'-O-i-Pro | H | H | 2 | 140–142.5 | Benz/Pet. Ether |
| 59 | 1 | 4'-i-Pro | H | H | 2 | 153–156 | Iprop/Ether |
| 60 | 2 | 2'-OME 3'-OMe | H | H | 3 | 238–240 | Alc./ |
| 61 | 2 | 2'-OMe 4'-OMe | H | H | 2 | 188–191 | Aq.Alc. |
| 62 | 2 | 2'-OMe 5'-OMe | H | H | 2 | 181–183 | " |

EXAMPLE 4

In a similar manner except that the cinnamoyl chloride used in Example 3 was replaced by the corresponding hydrocinnamoyl chloride, the following compounds could be prepared:

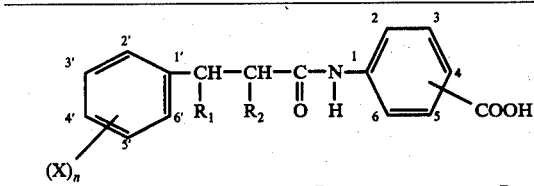

| Comp No. | n | X | $R_1$ | $R_2$ | Pos. COOH | M.P.(° C) | Recrys. Solvent |
|---|---|---|---|---|---|---|---|
| 63 | 1 | 3'-OMe | H | H | 2 | 192–194.5 | Aq.Alc. |
| 64 | 2 | 3'-OMe 4'-OMe | H | H | 3 | 176–177 | Alc./Benz. |
| 65 | 1 | 4'-Cl | H | H | 4 | 278.5–280.5 | Aq.Alc. |
| 66 | 1 | 4'-OMe | H | $CH_3$ | 4 | 222–226 | " |
| 67 | 2 | 3'-OMe 4'-OMe | H | H | 2 | 136–137.5 | Benzene |

EXAMPLE 5

4 Grams of 3,4-dimethoxycinnamic acid dissolved in 20 ml of dry pyridine. To this solution were added under cooling with ice and agitation 2 g of benzenesulfonyl chloride whereby a red orange precipitate was formed. The reaction mixture was stirred for about one hour and then 2 g of methyl anthranilate were added to the mixture under cooling with ice. The mixture was stirred for 2 hours at room temperature to complete the reaction. After completion of the reaction, the reaction mixture was concentrated and the residue was taken up in about 10 ml of chloroform. The solution was washed first with a 10 % aqueous solution of caustic soda, then with a 10% aqueous solution of hydrochloric acid and finally with water and then distilled to remove chloroform whereby crystals of N-(3', 4'-dimethoxycinnamoyl)-anthranilic acid methyl ester were obtained.

This product was dissolved in 10 m of ethanol. To this solution were added 10 ml of a 10 % aqueous solution of caustic soda and the mixture was warmed at 50° C to effect hydrolysis of the ester group. After completion of the reaction, the reaction liquid was concentrated approximately to ½ volume and poured into an aqueous solution of hydrochloric acid. The precipitated crystals were collected by filtration, wash with water and recrystallized from aqueous alcohol to obtain a yield of 48 % N(3', 4'-dimethoxy cinnamoyl)anthranilic acid having a melting point of 211°–213° C.

When the condensation reaction was carried out under similar conditions except that 1.9 g of anthranilic acid were used in place of methyl anthranilate used in this example, 2.0 g of N-(3', 4'-dimethoxycinnamoyl)anthranilic acid could directly be obtained.

EXAMPLE 6

2 Grams of 3,4-dimethoxycinnamic acid were dissolved in a mixture of 20 ml of dry dimethylformamide and 1.5 g of triethylamine. To this solution was added under ice cooling and agitation 1.1 g of ethyl chlorocarbonate and the mixture was then reacted for one hour. To this mixture were added 10 ml of dimethylformamide containing 1.5 g of 3-aminobenzoic acid and the mixture was stirred for 2 hours. After completion of the reaction, the reaction liquid was concentrated approximately to 1/2 volume and poured into an aqueous solution of hydrochloric acid. The precipitated crystals were separated by filtration, washed with water and recrystallized from an equivolume mixture of ethanol and water to obtain a yield of 50 % 3-(3', 4'-dimethoxycinnamoylamino)-benzoic acid having a melting point of 225°–226° C.

EXAMPLE 7

To a mixture of 20 ml of dioxane and 0.7 g of pyridine were added 2 g of 3,4-dimethoxycinnamic acid, 1.6 g of phosphorus oxychloride and 1.6 g of methyl anthranilate. The mixture was heated under reflux for 2 hours to effect reaction. After completion of the reaction, the reaction mixture was concentrated and the residue was dissolved with heating in ethanol and then cooled whereby crystals were precipitated. The crystals were separated by filtration and treated in a manner silimar to that described in Example 5 to effect hydrolysis of the ester group. The product was recrystallized from chloroform to obtain 2 g of N-(3', 4'-dimethoxycinnamoyl)-anthranilic acid having a melting point of 211°–213° C.

EXAMPLE 8

"Homologous Passive Cutaneous Anaphylaxis in Rats"

Wistar male rats weighing 120-150 g were used in this experiment. A reaginic antibody was obtained from rats immunized with egg albumin (EA) dissolved in the pertussis-diphtheria-tetanus vaccine. Normal rats were sensitized passively with dilution of the antibody by means of intradermal injection. After 48 hours of the sensitization, the mixture of antigen (EA) and evens blue was injected intravenously. The animals were killed by a blow on the head 30 minutes after the injection, and then the blue spot resulted from the antigen-antibody reaction was measured photometrically.

A given test compound dissolved in 1 % $NaHCO_3$ solution was administrated in a dose of 200 mg/kg orally 2 hours prior to the injection of antigen, while only the vehicle solution was administered to the control group. Chlorphenesin used as a positive control is generally well known as an inhibitor of mast cell disruption resulting from the allergic response.

The efficacy of the test compounds to inhibit the homologous passive cutaneous anaphlaxis was compared with the value (%) calculated using the following formula:

$$\frac{A - B}{A} \times 100$$

wherein A stands for the amount of leaked dye in control group and B for the amount of leaked dye in the group administered with a given test compound.

It seems likely that the homologous passive cutaneous anaphylaxis in rats is useful to determine whether a test compound inhibits an allergic response or not.

The results of the tests were as shown below.

| Test No. | Compound | Inhibition (%) |
|---|---|---|
| 1 | Control | 0 |
| 2 | Chlorphenesin | 36.7 |
| 3 | N-cinnamoyl-anthranilic acid | 16.7 |
| 4 | 3-(cinnamoylamino)-benzoic acid | 10.0 |
| 5 | 4-(cinnamoylamino)-benzoic acid | 7.0 |
| 6 | N-(4'-hydroxycinnamoyl)-anthranilic acid | 36.7 |
| 7 | 3-(3'-methoxycinnamoylamino)-benzoic acid | 45.0 |
| 8 | N-(2'-chlorocinnamoyl)-anthranilic acid | 60.2 |
| 9 | N-(4'-chlorocinnamoyl)-anthranilic acid | 69.4 |
| 10 | N-(4'-bromocinnamoylamino)-benzoic acid | 32.3 |
| 11 | N-(3'-fluorocinnamoyl)-anthranilic acid | 47.5 |
| 12 | N-(4'-methylcinnamoyl)-anthracilic acid | 54.0 |
| 13 | 4-(2'-hydroxy-3'-methoxycinnamoylamino)-benzoic acid | 33.5 |
| 14 | N-(2',3'-dimethoxycinnamoyl)-anthranilic acid | 56.8 |
| 15 | 3-(2',3'-dimethoxycinnamoylamino)-benzoic acid | 41.1 |
| 16 | N-(3'-methoxy-4'-n-propoxycinnamoyl)-anthranilic acid | 52.2 |
| 17 | N-(3'-methoxy-4'-isopropoxycinnamoyl)-anthranilic acid | 47.1 |
| 18 | N-(3',4'-dimethoxycinnamoyl)-anthranilic acid | 46.1 |
| 19 | N-(2',4',5'-trimethoxycinnamoyl)-anthranilic acid | 56.8 |
| 20 | N-(3',4'-dimethoxylhydrocinnamoyl)-anthranilic acid | 55.4 |
| 21 | N-(3',4'-dimethoxy-$\beta$-methylcinnamoyl)-anthranilic acid | 66.2 |
| 22 | N-[3'-methoxy-4'-(2,3-dihydroxypropoxy)-cinnamoyl]-anthranilic acid | 9.0 |
| 23 | N-(3'-methoxy-4'-carboxylmethoxy-cinnamoyl)-anthranilic acid | 0 |

The above results obviously show that in pharmacological activity, the new aromatic carboxylic amide derivatives of this invention are almost equal to or higher than Chlorphenesin. The nuclear-substituted cinnamoylaminobenzoic acid derivatives are generally stronger in the activity than the nuclear-unsubstituted cinnamoylaminobenzoic acid derivatives. However, the cinnamoylaminobenzoic acid derivatives nuclearly substituted by a hydrophilic group exhibit substantially no activity.

EXAMPLE 9

"Effect on the Disruption of the Sensitized Mast Cells"

Mesenteric mast cells isolated from normal rats were sensitized passively by means of incubation with rat reaginic antibody at 37° C. After termination of the incubation, the specific antigen (DNP-Ascaris) was added to the incubation medium, then these mast cells in mesentery were fixed with formalin and stained with 0.1 % toluidine blue (in acetic acid buffer; pH: 4.6). The number of mast cells disrupted as a consequence of the antigen-antibody reaction were counted under a microscope. The number of the mast cells disrupted were also counted without the addition of the specific antigen.

A given test compound dissolved in 1 % $NaHCO_3$ solution was added to the incubation medium at a concentration of $10^{-5}$ g/ml, 5 minutes prior to the treatment of antigen, while only the vehicle was added to the control group. Disodium cromoglycate used as positive control is generally well known as an inhibitor of mast cell disruption resulted in allergic response.

The efficacy of the test compounds to inhibit the mast cell disruption was compared with the value (%) calculated using the following formula:

$$\frac{(P - Q) - (R - Q)}{(P - Q)} \times 100$$

wherein P stands for the percentage of disrupted mast cells in the control group, Q for the percentage of mast cells disrupted spontaneously and R for the percentage of disrupted mast cells in the group treated with a given test compound.

It seems likely that this method is useful to determine whether a given test compound inhibits the disruption of mast cells and the subsequent release of chemical mediators from mast cells or not.

The results of the tests were as tabulated below.

| Test No. | Compound | Inhibition percentage |
|---|---|---|
| 1 | Control | 0 |
| 2 | Disodium cromoglycate | 16 |
| 3 | N-(3',4'-dimethoxycinnamoyl)-anthranilic acid | 33 |
| 4 | N-(3',4'-dimethoxy-$\beta$-methylcinnamoyl)-anthranilic acid | 45 |
| 5 | 3-(3'-methoxycinnamoylamino)-benzoic acid | 18 |
| 6 | N-(3'-methoxy-4'-n-propoxycinnamoyl)-anthranilic acid | 37 |

The above results obviously show that in pharmacological activity the novel aromatic carboxylic amide derivatives of this invention are equal to or higher than disodium cromoglycate.

EXAMPLE 10

"Experimental Asthma in Rats"

Twenty normal male rats weighing 120-150 g were divided into four groups each consisting of five rats. All of the rats were sensitized passively by means of intravenous injection of rat reaginic antibody. After a lapse of 22 hours of sensitization, 5 milliliters of a 1% aqueous solution of $NaHCO_3$ containing (3',4'-dimethoxycinnamoylamino)-benzoic acid* in a dose of 0 mg/kg (control), 5 mg/kg, 10 mg/kg and 20 mg/kg were orally administered to the rats in each group, and then canulation was begun on both the trachea and the common carotid artery on the rats. The rate and volume of respiration and systemic blood pressure were recorded simultaneously on a polygraph.

* Compound No. 33

After 2 hours of administration, the challenge symptoms were subjected, by means of injection of the antigen, and the results are shown in the drawing attached herewith. Asthmatic symptoms resulting from the challenge were observed in the control group only. As is evident from the drawing, decrease in the rate of respiration was observed in the control after a lapse of 3 minutes from the injection of the antigen. On the other hand, Compound No. 33 showed inhibition at a does of 5 mg/kg or more. Concerning the decrease in the volume of respiration, this compound showed inhibition in a does of 10 mg/kg or more. This compound showed no inhibiting effect on depression of blood pressure just after the challenge but showed an inhibiting effect on subsequent depression.

EXAMPLE 11

"Acute Toxicity"

The median lethal dose ($LD_{50}$) of the new aromatic carboxylic acid amide derivatives of this invention were determined in dd-stain male and female mice (6 weeks old) by oral administration and in Wistar strain male and female rats (7 weeks old) by oral and intraperitoneal administration. Each animal selected for the experiment was maintained in an air conditioned room at a temperature of 22° ± 1° C and a relative humidity of 55 ± 5% during the full course of the experiment. All animals were fed compressed pellets (CE-2 type produced by Japan CLEA Co.) and water was available ad libitum by bottle. Five groups of ten animals for each administration route were used.

Since these compounds were isoluble in water, they were suspended in a 0.5% aqueous solution of carboxymethylcellulose at each dosage level. The administrative volume of each agent to 10 g body weight mouse was 0.2 ml for oral administration, while that to 100g body weight of rat was 0.5 ml for intraperitoneal and oral administrations.

The $LD_{50}$ values were calculated from the mortality on the 8th day by the Litchfield-Wilcoxon's method. The results of the tests were as tabulated below.

| | | |
|---|---|---|
| N-(3',4'-dimethoxycinnamoyl)-anthranilic acid | | |
| Rats | 1850 mg/kg | (o.) |
| Rats | 2030 mg/kg | (o.) |
| | 385 mg/kg | (i.p.) |
| | 338 mg/kg | (i.p.) |
| Mice | 705 mg/kg | (o.) |
| | 500 mg/kg | (o.) |
| N-(2'-chlorocinnamoyl)-anthranilic acid | | |
| Mice | 343 mg/kg | (o.) |
| N-(4'-chlorocinnamoyl)-anthranilic acid | | |
| Mice | 551 mg/kg | (o.) |
| N-(3'-chlorocinnamoyl)-anthranilic acid | | |
| Mice | 700 mg/kg | (o.) |
| N-(2'-fluorocinnamoyl)-anthranilic acid | | |
| Mice | 321 mg/kg | (o.) |
| N-(3'-fluorocinnamoyl)-anthranilic acid | | |
| Mice | 551 mg/kg | (o.) |
| N-(4'-fluorocinnamoyl)-anthranilic acid | | |
| Mice | 481 mg/kg | (o.) |

As demonstrated in Examples 8, 9, 10 and 11, the new aromatic carboxylic amide derivatives and functional derivatives thereof of this invention serve to inhibit not only cutaneous anaphylaxie and release of chemical mediators from mast cells but also experimentally induced asthmatic cymptoms caused by an antigen-antibody reaction. These results obviously show that the derivatives of this invention are effective for the therapeutic treatment of allergic diseases including asthma, hay fever, urticaria and atopic dermatitis.

In accordance with this invention, there is provided a pharmaceutical composition consisting essentially of an aromatic carboxylic amide of the general formula (I) or a salt thereof in association with a pharmaceutical carrier or diluent. Compositions according to this invention are useful for the treatment of asthma. The composition is administered to the patient at regular intervals in order to inhibit the effects of asthmatic attack from which the patient may suffer. When employed in this manner, the unit dosage of the composition is preferably such that from 1 mg to 250 mg of active compound are administered to the patient at each administration. The total dosage for daily administration to an adult or a child contains 200 to 800 mg or 100 to 400 mg, respectively, of the active compound. This dosage may adequately be adjusted according to the symptoms.

The composition of this invention is prepared by mixing the active compound with a carrier or diluent conventionally used in medicamental compositions for oral or parenteral applications. Illustrative of such carriers and diluents are, for example, water, lactose, sucrose, starch, calcium stearate, talc, calcium carboxylmethylcellulose, crystalline cellulose and the like substances. If desired, the composition may be incorporated with a preserving agent, stabilizer, emulsifier, buffer and the like, as conventional in the art. The composition of this invention can be worked up to preparations containing the unit dosage of the active compound in the form of powder, pill, tablet, dragee, capsule, injection, suspended agent, ointment and suppository.

The pharmaceutical composition of this invention will be explained by way of examples. It is to be construed, however, that these examples are given only for the purpose of illustration and not for limiting the scope of this invention.

EXAMPLE 12

"Powdery Preparation"

10 Milligrams to 1.5 g of crystalline 2-(3',4'-dimethoxycinnamoylamino)-benzoic acid were blended with Indian corn starch and lactose in proportions shown in Table 1 to make the total weight to 5 g. The mixture was triturated in a mortar and the resultant powdery mixture was divided to prepare 10 packs of a powdery preparation.

Table 1

| Sample No. | 1 | 2 | 3 | 4 | 5 | 6 | 7 | 8 | 9 |
|---|---|---|---|---|---|---|---|---|---|
| Active comp. | 10 mg | 20mg | 50mg | 0.1g | 0.25g | 0.5g | 0.75g | 1g | 1.5g |
| Corn Starch | 4.29g | 4.28g | 4.25g | 4.2g | 4.1g | 3.9g | 3.7g | 3.5g | 3.1g |
| Lactose | 0.7g | 0.7g | 0.7g | 0.7g | 0.65g | 0.6g | 0.55g | 0.5g | 0.4g |

EXAMPLE 13

"Pills"

5-150 Grams of the same active compound as used in Example 12 were blended with Indian corn starch and lactose in proportions shown in Table 2 and then with 150 ml of a 2% aqueous solution of hydroxypropylcellulose and the mixture was kneaded, shaped into pills and dried. The resultant pills were subjected to a sieve treatment using a sieve of 12 mesh and the passed fraction smaller than this size was then subjected to further sieve treatment using a sieve of 42 mesh to remove any reamining fraction whereby pills were prepared.

Table 2

| Sample No. | 1 | 2 | 3 | 4 | 5 | 6 | 7 |
|---|---|---|---|---|---|---|---|
| Active Comp. | 5g | 10g | 25g | 50g | 75g | 100g | 150g |
| Corn Starch | 425g | 420g | 410g | 390g | 370g | 350g | 310g |
| Lactose | 67g | 67g | 62g | 57g | 52g | 47g | 37g |

EXAMPLE 14

"Tablets"

100 Grams of the same active compound as used in Example 12 were admixed with 95g of lactose and 40g of Indian corn starch and then with 700 ml of a 5% aqueous solution of hydroxypropylcellulose. The mixture was kneaded and then shaped into pills. Next, the pills were admixed with 8 g of calcium carboxylmethylcellulose and 3.5g of calcium stearate and the mixture was shaped into 1000 tablets.

EXAMPLE 15

"Dragees"

The tablets obtained in Example 14 were charged into a rotary coating tank. An ethanolic solution of purified shellac was added in an amount of 3 mg per tablet. Then, an aqueous suspension containing 6 mg of gelatin, 7 mg of gum arabic, 24 mg of talc, 122 mg of calcium carbonate (precipitated) and 73 g of white sugar for every tablet was charged into the rotary tank to apply a sugar coating onto the surface of the tablets. The coated tablets were then dried to prepare dragees.

EXAMPLE 16

"Film-coated tablets"

The tablets obtained in Example 14 were placed in a rotary coating tank and a 10% ethanolic solution of hydroxypropylmethylcellulose in an amount of 10 mg per tablet was added portionwise at 5 times to the tablets and the mixture was stirred and dried.

EXAMPLE 17

"Capsules"

5-150 Grams of the same active compound as used in Example 12 were thoroughly blended with lactose and Indian corn starch in amounts shown in Table 3. The mixture was admixed with talc, homogeneously mixed and then charged equally into 1000 hard capsules.

Table 3

| Sample No. | 1 | 2 | 3 | 4 | 5 | 6 | 7 |
|---|---|---|---|---|---|---|---|
| Active comp. | 5g | 10g | 25g | 50g | 75g | 100g | 150g |
| Lactose | 67g | 62g | 42g | 55g | 30g | 39g | 23g |
| Corn Starch | 25g | 25g | 25g | 30g | 30g | 35g | 40g |
| Talc | 3g | 3g | 3g | 5g | 5g | 6g | 7g |
| Total Weight | 100g | 100g | 100g | 140g | 140g | 180g | 220g |

EXAMPLE 18

"Syrupy Preparation"

Distilled water was added to white sugar and the mixture was heated until boiling to dissolve the white sugar in the water. To this solution were added 2-(3',4'-dimethoxycinnamoylamino)-benzoic acid, sodium carboxylmethylcellulose and ethyl p-hydroxybenzoate and the whole was mixed to prepare a syrupy preparation. The proportion of the ingredients in 1 ml of the syrup was as follows:

| | |
|---|---|
| Active compound | 10 mg |
| Sodium carboxymethylcellulose | 10 mg |
| White sugar | 740 mg |
| Ethyl p-hydroxybenzoate | 1 mg |
| Distilled water | to make the total volume to 1 ml |

EXAMPLE 19

"Cream preparation"

Stearyl alcohol was fused on a water bath. To the melt were added the same active compound as used in Example 18 and then Span 80 and liquid paraffin. The mixture was heated to 70° C and stirred to prepare a composition A. Separately, ethyl p-hydroxybenzoate and propyl p-hydroxybenzoate were dissolved in distilled water. Tween 80 and sodium lauryl sulfate were then dissolved and the mixture was heated to 70° C to prepare a composition B.

The composition B was added to the composition A under agitation and agitation was continued until the mixture was entirely cooled, whereby a creamy preparation was prepared. The composition of the ingredients in every 100 g of the cream was as follows:

| | |
|---|---|
| The active compound | 1g |
| Stearyl alcohol | 10 g |
| Liquid paraffin | 40 g |
| Sodium lauryl sulfate | 1 g |
| Span 80 | 5.5 g |
| Tween 80 | 2.5 g |
| Ethyl p-hydroxybenzoate | 25 mg |
| Propyl p-hydrobenzoate | 15 mg |
| Distilled water | to make the total amount to 100 g |

EXAMPLE 20

"Suppository"

160 Grams of Carbowax 4000 and 40 g of Carbowax 1500 were mixed under heating. To the mixture were added with stirring 15 g of the same active compound as in Example 18 and the whole was thoroughly mixed. The mixture was then cast equally into 100 molds well cooled. After about 15 minutes, solidified materials were taken out from the molds whereby suppositories were obtained.

EXAMPLE 21

"Clinical trial for adults"

A clinical trial was made by administering 2-(3',40'-dimethoxycinnamoylamino)-benzoic acid orally to adult patients having asthma bronchiale. These patients having asthma bronchiale were chosen from those suffering from atopic and mixed forms. Determination of the effect were integrally judged from the extent of subjective symptoms (the number of asthma attacks, the degree of dyspnea, wheeze, the number of cough attacks and sputum expectoration), objective findings (dry rale) and pulmonary function test.

The effect was evaluated by five grades of "remarkable improvement", "moderate improvement", "slight improvement", "unchanged", and "aggravated". A daily dose (400–600 mg) of the active compound in the powdery preparation obtained in Example 12 was administered orally to patients in equal portions four times daily, ie, after every meal and before sleeping. The results were shown in Table 4 below.

Table 4

| Name of Patient | Age | Body Weight(kg) | Severity | Administrn. dose × days | Side effect | Evaluation |
|---|---|---|---|---|---|---|
| S.K. | 58 | 56 | moderate | 600mg × 14 | none | slight imp. |
| K.N. | 44 | 61 | moderate | 600mg × 14 | none | mod. impr. |
| T.M. | 18 | 63 | moderate | 400mg × 21 | none | mod. impr. |
| Y.I. | 39 | — | moderate | 600mg × 21 | none | unchanged |
| K.M. | 44 | 51 | moderate | 400mg × 21 | none | mod. impr. |
| M.M. | 21 | 41 | merious | 400mg × 14 | none | slight imp. |
| K.K. | 24 | 43 | moderate | 600mg × 24 | none | mod. impr. |
| I.G. | 16 | 50 | moderate | 600mg × 20 | none | unchanged |

EXAMPLE 22

"Clinical trial for children"

A clinical trial was made by orally administering Compound No. 33 to child patients having asthma bronchiale. Child patients having asthma bronchiale in atopic and mixed forms were chosen for the clinical trial. Determination of the effect was integrally judged from the extent of subjective symptoms (the number of asthma attacks, the degree of dyspnea, wheeze, the number of cough attacks and sputum expectoration), objective findings (dry rale) and pulmonary function test.

The effect was evaluated by five grades of "remarkable improvement", "moderate improvement", "slight improvement", "unchanged" and "aggravated". A daily dose (100–200 mg) of the active compound in the powdery preparation obtained in Example 12 was administered orally to patients in equal portions four times a day, i.e., after every meal and before sleeping. The results were as shown in Table 5 below.

Table 5

| Name of Patient | Age | Body Weight(kg) | Severity | Administrn. dose × days | Side effect | Evaluation |
|---|---|---|---|---|---|---|
| Y.K. | 12 | unkn. | moderate | 200 mg × 15 | none | mod. impr. |
| M.K. | 11 | 27.4 | moderate | 200 mg × 29 | none | slight impr. |
| H.I. | 10 | 27 | moderate | 200 mg × 35 | none | slight imp. |
| K.O. | 11 | 46.5 | slight | 200 mg × 15 | none | mod. impr. |
| T.K. | 9 | 22.5 | moderate | 200 mg × 15 | none | mod. impr. |

What is claimed is:

1. A pharmaceutical composition for alleviating the symptoms of allergic reactions in mammals when administered in an effective amount consisting essentially of a mixture of an active ingredient selected from the group consisting of an aromatic carboxylic amide derivative of the formula:

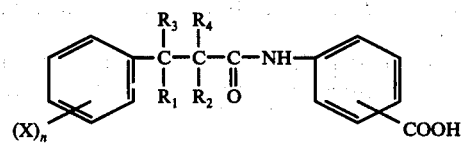

and the therapeutically acceptable salts thereof, wherein $R_1$ and $R_2$ are each selected from the group consisting of a hydrogen atoms and an alkyl group having 1–4 carbon atoms, $R_3$ and $R_4$ each represent a hydrogen atom or may be combined together to form another chemical bond, each X is an alkoxyl group having 1–4 carbon atoms and may be the same or different, and $n$ is an integer from 2 to 3 and at least one pharmaceutically acceptable carrier or diluent.

2. A pharmaceutical composition as in claim 1 containing said active ingredient in an amount in the range of about 1–250 mg per unit dosage.

3. The pharmaceutical composition of claim 1 wherein said active ingredient is N-(3',4'-dimethoxycinnamoyl)-anthranilic acid.

4. The pharmaceutical composition of claim 1 wherein said active ingredient is N-(3',4'-dimethoxy-β-methylcinnamoyl)-anthranilic acid.

5. The pharmaceutical composition of claim 1 wherein said active ingredient is N-(3'-methoxy-4'-n-propoxycinnamoyl)-anthranilic acid.

6. A method of alleviating the symptoms of allergic reactions in mammals characterized by administering orally a therapeutically effective amount of a compound selected from the group consisting of an aromatic carboxylic amide derivative of the formula:

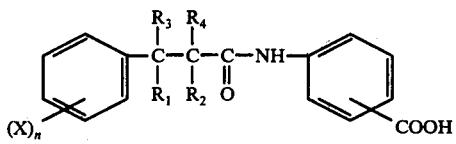

and the therapeutically acceptable salts thereof, wherein $R_1$ and $R_2$ are each selected from the group consisting of a hydrogen atom and an alkyl group having 1–4 carbon atoms, $R_3$ and $R_4$ each represent a hydrogen atom or may be combined together to form another chemical bond, one or more X's may be the same or different and are selected from the group consisting of a hydroxyl group, a halogen atom, an alkyl group having 1–4 carbon atoms and an alkoxyl group having 1–4 carbon atoms, and $n$ is an integer from 1 to 3, provided that when X's stand for two alkyl or alkoxyl groups, the alkyl groups thereof may be connected together into an alkylene group.

7. The method of claim 6 wherein said compound is a nuclear-substituted cinnamic amide of the general formula:

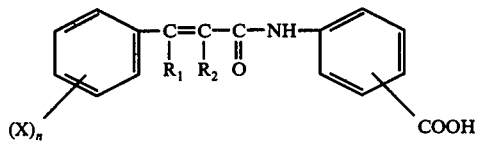

wherein $R_1$, $R_2$ have the same meanings as in claim 2, X is an alkoxyl group having 1–4 carbon atoms, $n$ is an integer of 2–3 and the therapeutically acceptable salts thereof.

8. The method of claim 7 wherein both $R_1$ and $R_2$ are hydrogen atoms.

9. The method of claim 7 wherein at least one of $R_1$ and $R_2$ is an alkyl group having 1–4 carbon atoms.

10. The method of claim 6 wherein said compound is a nuclear-substituted phenylpropionamide of the general formula:

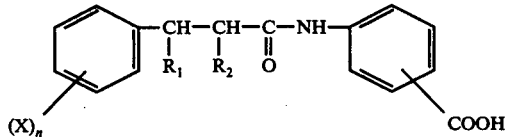

wherein $R_1$, $R_2$ have the same meanings as in claim 2, X is an alkoxyl group having 1–4 carbon atoms, $n$ is an integer of 2-3, and the therapeutically acceptable salts thereof.

11. The method of claim 10 wherein both $R_1$ and $R_2$ are hydrogen atoms.

12. The method of claim 10 wherein at least one of $R_1$ and $R_2$ is an alkyl group having 1–4 carbon atoms.

13. The method of claim 6 wherein said compound is N-(3′,4′-dimethoxycinnamoyl)-anthranilic acid.

14. The method of claim 6 wherein said compound is N-(3′,4′-dimethoxy-β-methylcinnamoyl)-anthranilic acid.

15. The method of claim 6 wherein said compound is N-(3′-methoxy-4′-n-propoxycinnamoyl)-anthranilic acid.

16. The method of claim 13 wherein said symptoms of said allergic reactions are due to hay fever.

17. The method of claim 13 wherein said symptoms of said allergic reactions are due to atopic dermatitis.

18. The method of claim 13 wherein said symptoms of said allergic reactions are due to urticaria.

19. A method for the treatment of asthma, characterized by administering a compound selected from group consisting of an aromatic carboxylic amide derivative of the formula:

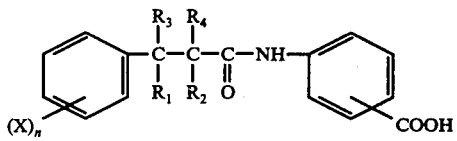

and therapeutically acceptable salts thereof, wherein $R_1$ and $R_2$ are each selected from the group consisting of a hydrogen atom and an alkyl group having 1–4 carbon atoms, $R_3$ and $R_4$ each represent a hydrogen atom or may be combined together to form another chemical bond, one or more X's may be the same or different and are selected from the group consisting of a hydroxyl group, a halogen atom, an alkyl group having 1–4 carbon atoms and an alkoxyl group having 1–4 carbon atoms, and $n$ is an integer from 1 to 3, provided that when X's stand for two alkyl or alkoxyl groups, the alkyl group thereof may be connected together into an alkylene group, in a daily dose of 200–800 mg or 50–300mg to adults and children, respectively.

20. The method of claim 19 wherein said compound is N-(3′,4′-dimethoxylcinnamoyl)-anthranilic acid.

* * * * *